US008729032B2

(12) United States Patent
Nagai et al.

(10) Patent No.: US 8,729,032 B2
(45) Date of Patent: May 20, 2014

(54) SELF-ASSEMBLING PEPTIDE AND PEPTIDE GEL WITH HIGH STRENGTH

(75) Inventors: Yusuke Nagai, Kasugai (JP); Hidenori Yokoi, Kasugai (JP); Koji Uesugi, Kasugai (JP); Keiji Naruse, Okayama (JP)

(73) Assignees: Menicon Co., Ltd., Nagoya-shi (JP); National University Corporation Okayama University, Okayama-shi (JP)

( * ) Notice: Subject to any disclaimer, the term of this patent is extended or adjusted under 35 U.S.C. 154(b) by 207 days.

(21) Appl. No.: 13/255,457

(22) PCT Filed: Feb. 12, 2010

(86) PCT No.: PCT/JP2010/052047
§ 371 (c)(1),
(2), (4) Date: Sep. 8, 2011

(87) PCT Pub. No.: WO2010/103887
PCT Pub. Date: Sep. 16, 2010

(65) Prior Publication Data
US 2012/0058066 A1  Mar. 8, 2012

(30) Foreign Application Priority Data
Mar. 9, 2009  (JP) .................................. 2009-054983

(51) Int. Cl.
*A61K 38/10*  (2006.01)
*C07K 7/08*  (2006.01)

(52) U.S. Cl.
CPC ...................................... *A61K 38/10* (2013.01)
USPC .......... 514/21.4; 514/21.5; 514/3.2; 530/325; 530/326; 530/327

(58) Field of Classification Search
None
See application file for complete search history.

(56) References Cited

U.S. PATENT DOCUMENTS

| 5,670,483 | A | 9/1997 | Zhang |
| 7,179,784 | B2 | 2/2007 | Zhang et al. |
| 8,299,032 | B2 * | 10/2012 | Yokoi et al. .................. 514/21.4 |
| 2006/0084607 | A1 | 4/2006 | Spirio et al. |
| 2006/0154852 | A1 | 7/2006 | Boden et al. |
| 2010/0016548 | A1 | 1/2010 | Yokoi et al. |

FOREIGN PATENT DOCUMENTS

| JP | 2008 505919 | 2/2008 |
| WO | WO 2004/007532 A2 | 1/2004 |
| WO | WO 2006/014570 A2 | 2/2006 |
| WO | 2007/000979 | 1/2007 |

OTHER PUBLICATIONS

Guo et al ("Prediction of Peptide Retention Times in Reversed-Phase High-Performance Liquid Chromatography" (1986) Journal of Chromatography 359: 519-532).*
Extended European Search Report issued Jun. 4, 2012 in Patent Application No. 10750643.8.
Third Party Observation dated Apr. 26, 2013 in European Application No. 10750643.8.
Guo, D., et al., "Prediction of Peptide Retention Times in Reversed-Phase High-Performance Liquid Chromatography," Journal of Chromatography, vol. 359, pp. 519-532, (1986).
Nagai, Y., et al., "Development of new peptide scaffold for 3-D cell culturing under mechanical stimulation," the Japan Society of Mechanical Engineers, p. 219, (Jan. 8, 2010).
International Search Report issued May 11, 2010 in PCT/JP10/052047 filed Feb. 12, 2010.

* cited by examiner

*Primary Examiner* — Karlheinz R Skowronek
*Assistant Examiner* — Mindy Newman
(74) *Attorney, Agent, or Firm* — Oblon, Spivak, McClelland, Maier & Neustadt, L.L.P.

(57) ABSTRACT

Provide are a peptide gel with practically sufficient mechanical strength and a self-assembling peptide capable of forming the peptide gel. The self-assembling peptide is formed of the following amino acid sequence: $a_1b_1c_1b_2a_2b_3db_4a_3b_5c_2b_6a_4$ where: $a_1$ to $a_4$ each represent a basic amino acid residue; $b_1$ to $b_6$ each represent an uncharged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue.

13 Claims, 12 Drawing Sheets

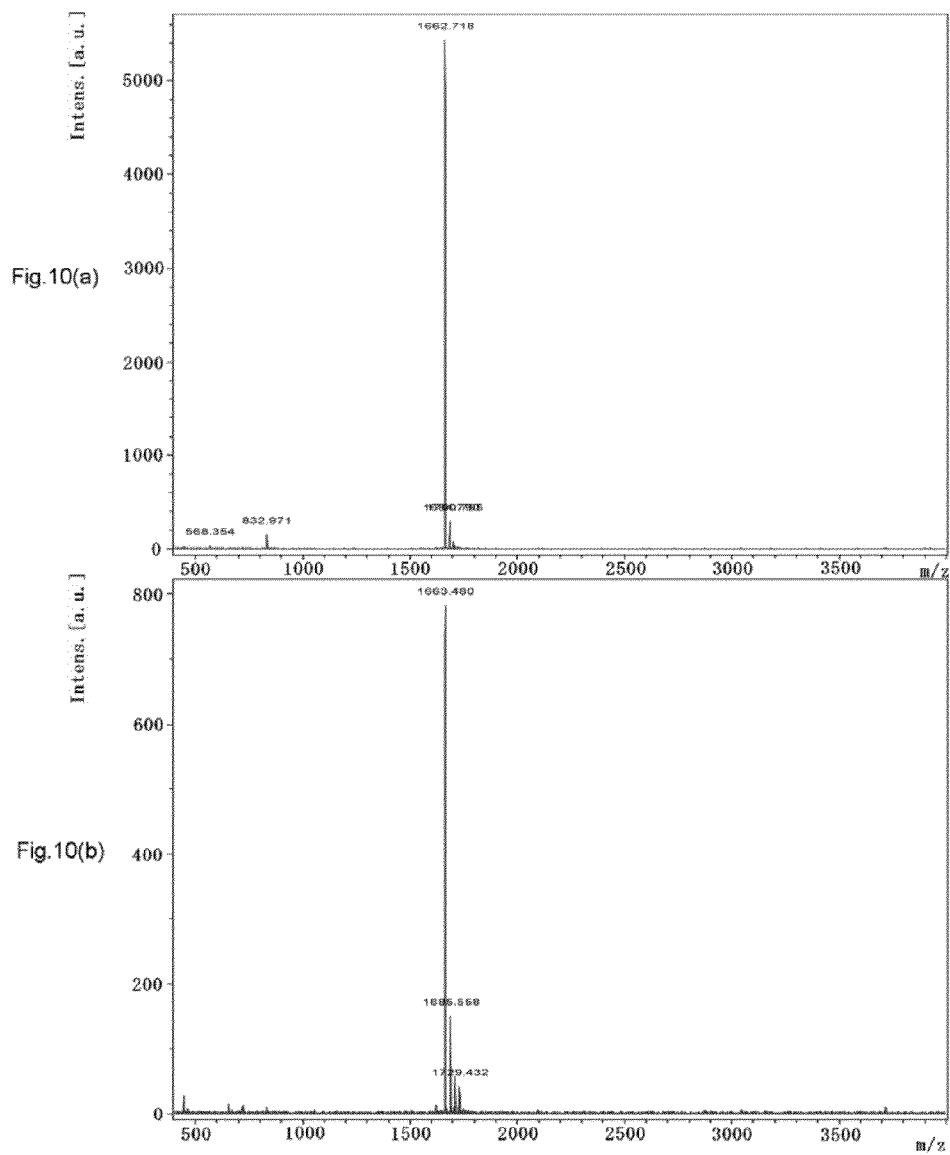

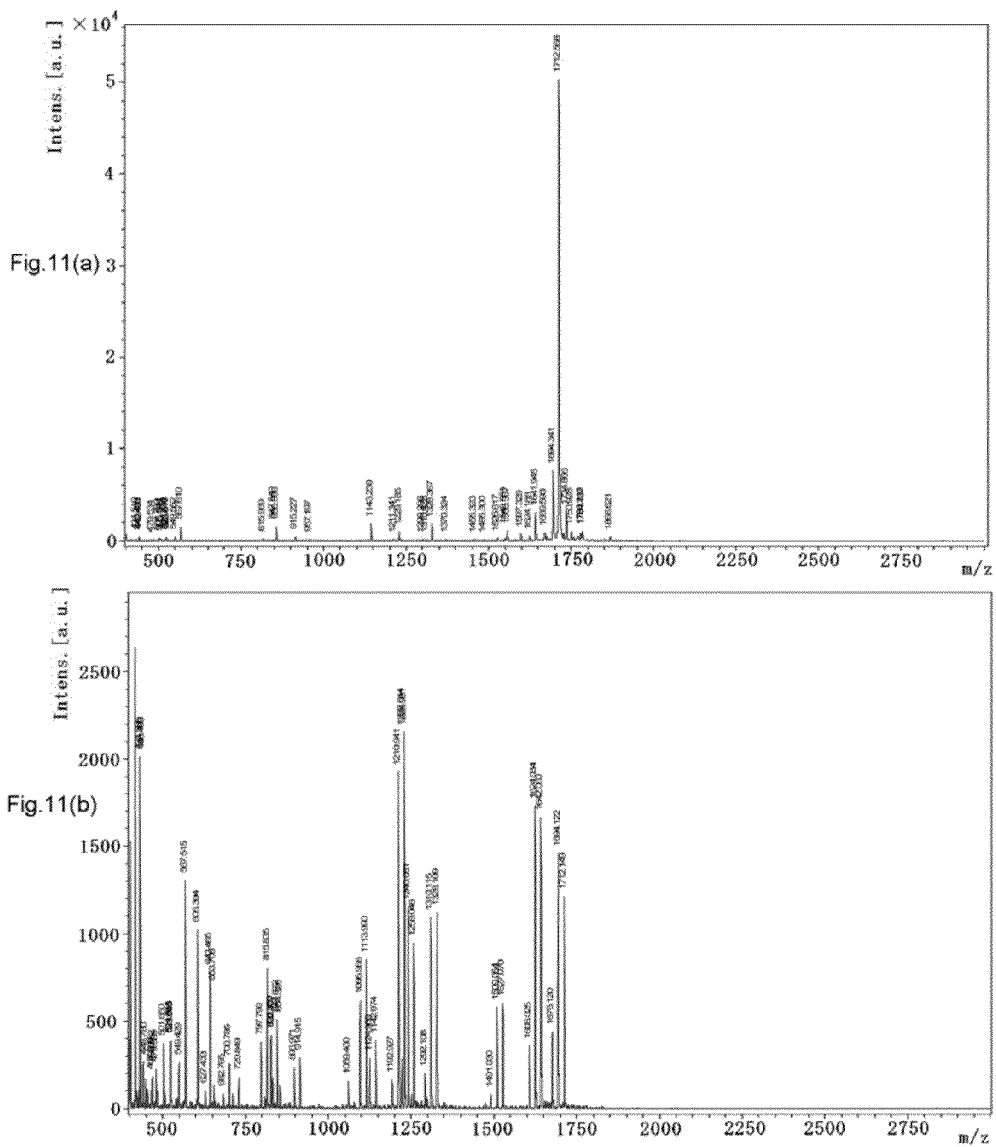

US 8,729,032 B2

```
                        SEQUENCE LISTING

<160> NUMBER OF SEQ ID NOS: 40

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 1

Arg Leu Asp Leu Arg Leu Ala Leu Arg Leu Asp Leu Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 2

Arg Leu Asp Leu Arg Leu Leu Leu Arg Leu Asp Leu Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 3

Arg Leu Asp Leu Arg Leu Ala Leu Arg Leu Asp Leu Arg Leu
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      self-assembling peptide
```

```
<400> SEQUENCE: 4

Arg Ala Ser Ala Arg Ala Asp Ala Arg Ala Asp Ala Arg Ala Ser Ala
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 5

Arg Ala Ser Ala Arg Ala Asp Ala Arg Ala Ser Ala Arg Ala Asp Ala
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 6

Arg Ala Asp Leu Arg Leu Ala Leu Arg Leu Asp Leu Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 7

Arg Leu Asp Leu Arg Leu Ala Leu Arg Leu Asp Ala Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 8

Arg Ala Asp Leu Arg Leu Leu Leu Arg Leu Asp Leu Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 9

Arg Ala Asp Leu Arg Leu Leu Leu Arg Leu Asp Ala Arg
1               5                   10

<210> SEQ ID NO 10
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      self-assembling peptide

<400> SEQUENCE: 10

Arg Leu Asp Leu Arg Ala Leu Leu Arg Leu Asp Leu Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 11

Arg Leu Asp Leu Arg Leu Leu Ala Arg Leu Asp Leu Arg
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      self-assembling peptide

<400> SEQUENCE: 12

Arg Gly Asp Asn Arg Leu Asp Leu Arg Leu Ala Leu Arg Leu Asp Leu
1               5                   10                  15

Arg

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Asp Ala Arg Ala Ala Ala Arg Ala Asp Ala Arg
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Glu Asp Val
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Leu Asp Val
```

```
1               5

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Glu Lys Pro Gly Ser Pro Pro Arg Glu Val Val Pro Arg Pro Arg
1               5                   10                  15

Pro Gly Val

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Asn Asn Gln Lys Ser Glu Pro Leu Ile Gly Arg Lys
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ile Gly Ser Arg
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Asn Ile Ala Glu Leu Leu Lys Asp Ile
1               5                   10

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Tyr Val Val Leu Pro Arg Pro Val Cys Phe Glu Lys Gly Met Asn
1               5                   10                  15

Tyr Thr Val Arg
            20

<210> SEQ ID NO 21
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Lys Val Ala Val
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Asp Ser Gly Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Arg Gly Asp Ser Pro Ala Ser Ser
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Gly Asp Asn
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Asp Phe
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Gly Asp Thr
1
```

```
<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Gly Asp Ala
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Gly Asp Ser
1

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Pro Lys Lys Lys Arg Lys Val
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Ala Ala Lys Arg Val Lys Leu Asp
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Gln Pro Lys Lys Lys Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Gln Arg Lys Arg Gln Lys
1               5

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Met Ser Phe Val Ser Leu Leu Leu Val Gly Ile Leu Phe Trp Ala
1               5                   10                  15

Thr Glu Ala Glu Gln Leu Thr Leu Cys Glu Val Phe Gln
            20                  25

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Leu Ser Leu Arg Gln Ser Ile Arg Phe Phe Leu Pro Ala Thr Arg
1               5                   10                  15

Thr Leu Cys Ser Ser Arg Tyr Leu Leu
            20                  25

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 35

Arg Leu Asp Leu Arg Leu Ala Leu Arg Leu Asp Leu Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 36

Arg Leu Asp Leu Arg Leu Leu Leu Arg Leu Asp Leu Arg
1               5                   10

<210> SEQ ID NO 37
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 37

Arg Leu Asp Leu Arg Leu Ala Leu Arg Leu Asp Leu Arg Leu
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 38

Arg Ala Ser Ala Arg Ala Asp Ala Arg Ala Asp Ala Arg Ala Ser Ala
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 39

Arg Ala Ser Ala Arg Ala Asp Ala Arg Ala Ser Ala Arg Ala Asp Ala
1               5                   10                  15

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term CH3CO
<220> FEATURE:
<223> OTHER INFORMATION: C-term NH2

<400> SEQUENCE: 40

Arg Gly Asp Asn Arg Leu Asp Leu Arg Leu Ala Leu Arg Leu Asp Leu
1               5                   10                  15

Arg
```

SELF-ASSEMBLING PEPTIDE AND PEPTIDE GEL WITH HIGH STRENGTH

CROSS-REFERENCE TO RELATED APPLICATIONS

The present application is a 35 U.S.C. §371 National Stage patent application of International patent application PCT/JP2010/052047, filed on Feb. 12, 2010, which claims priority to Japanese patent application JP 2009-054983, filed on Mar. 9, 2009.

TECHNICAL FIELD

The present invention relates to a self-assembling peptide capable of forming a high-strength peptide gel, and a peptide gel, which is formed from the peptide.

BACKGROUND ART

A collagen gel is generally used as a scaffold (scaffold for cells) to be used in research and actual therapy in the regenerative medicine field. However, the collagen gel is derived from an animal and hence may cause an unknown infectious disease. As means for eliminating the concern about the unknown infectious disease, there exists a scaffold derived from a chemically synthesized material. Examples of such material include a self-assembling peptide disclosed in Patent Document 1 or Patent Document 2. However, a scaffold (peptide gel) formed of the self-assembling peptide of Patent Document 1 or 2 is insufficient in mechanical strength and hence involves such a problem in handleability that the scaffold may collapse when grasped with tweezers, for example. Further, the self-assembling peptide gel of Patent Document 1 involves such a problem that the gel is insufficient in transparency at neutral pH environment.

PRIOR ART DOCUMENTS

Patent Documents
[Patent Document 1] U.S. Pat. No. 5,670,483A
[Patent Document 2] WO 2007/000979A1

SUMMARY OF INVENTION

Problems to be Solved by the Invention

The present invention has been made in order to solve the above-mentioned problem. An object of the present invention is to provide a peptide gel with practically sufficient mechanical strength and a self-assembling peptide capable of forming the peptide gel.

Means for Solving the Problems

According to the present invention, a self-assembling peptide is provided. The self-assembling peptide is formed of the following amino acid sequence:

Amino acid sequence: $a_1b_1c_1b_2a_2b_3db_4a_3b_5c_2b_6a_4$ where: $a_1$ to $a_4$ each represent a basic amino acid residue; $b_1$ to $b_6$ each represent an uncharged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue.

In one embodiment of the invention, $b_3$ and $b_4$ in the amino acid sequence each represent a hydrophobic amino acid residue.

In another embodiment of the invention, all of $b_1$ to $b_6$ in the amino acid sequence each represent a hydrophobic amino acid residue.

In still another embodiment of the invention, $b_1$ to $b_6$ in the amino acid sequence each independently represent an alanine residue, a valine residue, a leucine residue, or an isoleucine residue.

In still another embodiment of the invention, d in the amino acid sequence represents an alanine residue, a valine residue, a leucine residue, or an isoleucine residue.

In still another embodiment of the invention, the self-assembling peptide includes a peptide formed of an amino acid sequence of RLDLRLALRLDLR (SEQ ID NO: 1), RLDLRLLLRLDLR (SEQ ID NO: 2), RADLRLALRLDLR (SEQ ID NO: 6), RLDLRLALRLDAR (SEQ ID NO: 7), RADLRLLLRLDLR (SEQ ID NO: 8), RADLRLLLRLDAR (SEQ ID NO: 9), RLDLRALLRLDLR (SEQ ID NO: 10), or RLDLRLLARLDLR (SEQ ID NO: 11).

In still another embodiment of the invention, the self-assembling peptide includes a peptide formed of an amino acid sequence of RLDLRLALRLDLR(SEQ ID NO: 1) or RLDLRLLLRLDLR(SEQ ID NO: 2).

According to another aspect of the invention, a modified peptide is provided. The modified peptide includes the self-assembling peptide whose N-terminal amino group and/or C-terminal carboxyl group are/is modified and has a self-assembling ability.

In one embodiment of the invention, the N-terminal amino group and/or the C-terminal carboxyl group have/has added thereto an amino acid sequence including RGD.

According to still another aspect of the invention, a peptide gel is provided. The peptide gel is formed from an aqueous solution including the self-assembling peptide and/or the modified peptide.

In one embodiment of the invention, the aqueous solution further includes an additive.

In another embodiment of the invention, the additive includes at least one selected from the group consisting of a pH adjuster, an amino acid, a vitamin, a saccharide, a polysaccharide, an alcohol, a polyalcohol, a pigment, a bioactive substance, an enzyme, an antibody, DNA, and RNA.

In still another embodiment of the invention, the peptide gel has an absolute value L (g/s) of an amount of change in load per unit time of 0.03 g/s or more in an approximate straight line of values measured from the start of compression to between 8 and 10 seconds in a compression test carried out at a compression speed of 0.05 mm/s using a jig whose tip has a spherical shape with a diameter of 3.2 mm and a curvature radius of 1.6 mm under a temperature condition of 22° C.

According to still another aspect of the invention, a substrate for cell culture is provided. The substrate for cell culture includes at least one selected from the group consisting of the self-assembling peptide, the modified peptide, and the peptide gel.

According to still another aspect of the invention, a manufacturing method for a sterile peptide is provided. The manufacturing method for a sterile peptide includes the step of sterilizing the self-assembling peptide and/or the modified peptide under a pressurized condition at 100° C. or more.

According to still another aspect of the invention, a manufacturing method for an article coated with a peptide gel is provided. The manufacturing method for an article coated with a peptide gel includes the steps of: freezing the peptide gel; melting the frozen peptide gel to provide a peptide sol;

coating at least part of a surface of an article to be coated with the peptide sol; and reconstructing a peptide gel from the peptide sol.

Advantageous Effects of Invention

According to the self-assembling peptide having a specific amino acid sequence of the present invention, the peptide gel with practical mechanical strength may be obtained.

BRIEF DESCRIPTION OF DRAWINGS

FIG. 10(a) shows the mass spectrometry results of a peptide aqueous solution before sterilization treatment, and FIG. 10(b) shows the mass spectrometry results of the peptide aqueous solution after sterilization treatment.

FIG. 11(a) shows the mass spectrometry results of a trade name "PuraMatrix™" (manufactured by 3-D Matrix, Ltd.) before sterilization treatment, and FIG. 11(b) shows the mass spectrometry results of the trade name "PuraMatrix™" (manufactured by 3-D Matrix, Ltd.) after sterilization treatment.

DESCRIPTION OF EMBODIMENTS

Figure 1:
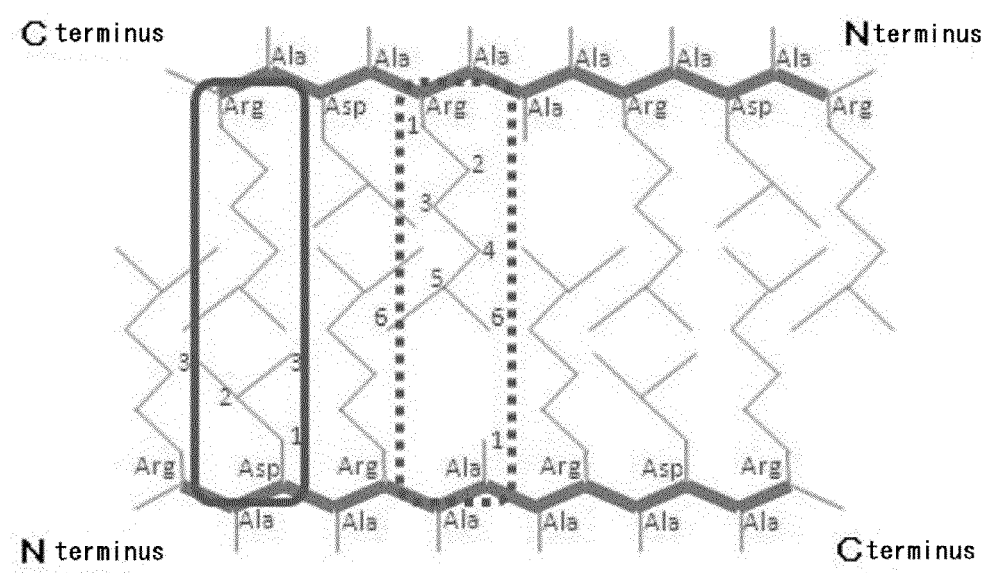
FIG. 1 is a schematic view for describing a distance between peptides each formed of a sequence of n-RADARAAARADAR-c (SEQ ID NO: 13). The bold line in a main chain connecting the N-terminus and the C-terminus in the figure represents a peptide bond.

A. Definition of Terms (1) The term "self-assembling peptide" as used herein refers to a peptide that assembles spontaneously via an interaction between peptide molecules in a solvent. Examples of the interaction include, but not particularly limited to, a hydrogen bond, an interionic interaction, an electrostatic interaction such as van der Waals force, and a hydrophobic interaction. In one embodiment, the self-assembling peptides are capable of self-assembling to form nanofibers, which further form a gel in an aqueous solution (for example, a 0.4 w/v % peptide aqueous solution) at room temperature.

(2) The term "gel" as used herein refers to a viscoelastic substance having both of viscous property and elastic property.

(3) The term "hydrophilic amino acid" as used herein encompasses basic amino acids such as arginine (Arg/R), lysine (Lys/K), and histidine (His/H), acidic amino acids such as aspartic acid (Asp/D) and glutamic acid (Glu/E), and uncharged polar amino acids such as tyrosine (Tyr/Y), serine (Ser/S), threonine (Thr/T), asparagine (Asn/N), glutamine (Gln/Q), and cysteine (Cys/C). The alphabetical letters in parentheses in the foregoing denote the three-letter code and single-letter code of the amino acid, respectively.

(4) The term "hydrophobic amino acid" as used herein encompasses nonpolar amino acids such as alanine (Ala/A), leucine (Leu/L), isoleucine (Ile/I), valine (Val/V), methionine (Met/M), phenylalanine (Phe/F), tryptophan (Trp/W), glycine (Gly/G), and proline (Pro/P). The alphabetical letters in parentheses in the foregoing denote the three-letter code and single-letter code of the amino acid, respectively.

B. Self-Assembling Peptide

A self-assembling peptide of the present invention is formed of the following amino acid sequence:

Amino acid sequence: $a_1b_1c_1b_2a_2b_3db_4a_3b_5c_2b_6a_4$ where: $a_1$ to $a_4$ each represent a basic amino acid residue; $b_1$ to $b_6$ each represent an uncharged polar amino acid residue and/or a hydrophobic amino acid residue, provided that at least five thereof each represent a hydrophobic amino acid residue; $c_1$ and $c_2$ each represent an acidic amino acid residue; and d represents a hydrophobic amino acid residue.

In general, it is estimated that the self-assembling peptide forms a β-sheet structure having a plane in which a hydrophilic side chain is disposed and a plane in which a hydrophobic side chain is disposed in an aqueous solution and that a plurality of peptide molecules assemble spontaneously through interactions such as a hydrogen bond or an interionic interaction acting on hydrophilic planes and a hydrophobic interaction acting on hydrophobic planes. Therefore, it has been regarded as very important for a conventional self-assembling peptide to have a hydrophilic amino acid and a hydrophobic amino acid alternately arranged at an equal ratio (see, for example, Patent Document 1).

On the other hand, as described above, the self-assembling peptide of the present invention is formed of an amino acid sequence of 13 residues having basic amino acid residues (at positions 1, 5, 9, and 13) and acidic amino acid residues (at positions 3 and 11) every other residue at symmetric positions in the N-terminal direction and the C-terminal direction with respect to a hydrophobic amino acid residue at position 7 in the center. That is, one feature of the self-assembling peptide of the present invention resides in that the self-assembling peptide does not have a hydrophilic amino acid and a hydrophobic amino acid alternately. Further, another feature of the self-assembling peptide of the present invention resides in that the self-assembling peptide does not have a hydrophilic amino acid residue and a hydrophobic amino acid residue at an equal ratio. Further, still another feature of the self-assembling peptide of the present invention resides in that the self-assembling peptide has four basic amino acid residues and two acidic amino acid residues at given symmetric positions with respect to a hydrophobic amino acid residue at position 7 in the center, and both of amino acid residues at the N-terminus and the C-terminus are basic amino acid residues. The hydrophobic amino acid residue at position 7 is a disadvantage for the formation of a β-sheet structure and makes a ratio between a hydrophilic amino acid and a hydrophobic amino acid unequal. Therefore, in general, this has been considered as adversely affecting the self-assembling ability of a peptide. However, the self-assembling peptide of the present invention has an excellent self-assembling ability and is capable of forming a peptide gel more excellent in mechanical strength than ever before. Although the reason why such effect is exerted is not clear, a possible reason is as described below. The self-assembling peptide of the present invention not only has a hydrophobic amino acid at position 7 but also has basic amino acid residues and acidic amino acid residues in which the number of the basic amino acid residues is larger than the number of the acidic amino acid residues by two and has the respective amino acid residues at specific positions. As a result, an electrostatic attractive force and an electrostatic repulsive force act on peptide molecules at an extremely excellent balance while an ability to form a β-sheet structure is maintained.

An amino acid that constructs the self-assembling peptide may be an L-amino acid or a D-amino acid. Further, the amino acid may be a natural amino acid or a non-natural amino acid. Of those, a natural amino acid is preferred because it is available at a low price and facilitates peptide synthesis.

In the amino acid sequence, $a_1$ to $a_4$ each represent a basic amino acid residue. A basic amino acid is preferably arginine, lysine, or histidine, more preferably arginine or lysine. This is because those amino acids have strong basicity. $a_1$ to $a_4$ may represent the same amino acid residue or different amino acid residues.

In the amino acid sequence, $b_1$ to $b_6$ each represent an uncharged polar amino acid residue and/or a hydrophobic amino acid residue, and at least five thereof each represent a hydrophobic amino acid residue. A hydrophobic amino acid is preferably alanine, leucine, isoleucine, valine, methionine, phenylalanine, tryptophan, glycine, or proline. An uncharged polar amino acid is preferably tyrosine, serine, threonine, asparagine, glutamine, or cysteine. This is because those amino acids are easily available.

$b_3$ and $b_4$ each independently represent preferably any appropriate hydrophobic amino acid residue, more preferably a leucine residue, an alanine residue, a valine residue, or an isoleucine residue, particularly preferably a leucine residue or an alanine residue. In the amino acid sequence, when $b_3$ and $b_4$, which are located at positions 6 and 8, respectively, each represent a hydrophobic amino acid residue, three amino acid residues at positions 6 to 8 are consecutively hydrophobic amino acid residues. It is estimated that a hydrophobic region formed in the center of the amino acid sequence as described above is capable of contributing to the formation of a peptide gel excellent in strength through its hydrophobic interaction and the like.

All of $b_1$ to $b_6$ each preferably represent a hydrophobic amino acid residue. This is because the self-assembling peptide is capable of suitably forming a β-sheet structure and self-assembling. $b_1$ to $b_6$ each independently represent more preferably a leucine residue, an alanine residue, a valine residue, or an isoleucine residue, still more preferably a leucine residue or an alanine residue. In a preferred embodiment, four or more of $b_1$ to $b_6$ each represent a leucine residue, it is particularly preferred that five or more thereof each represent a leucine residue, and it is most preferred that all thereof each represent a leucine residue. This is because a self-assembling peptide that is excellent in water solubility and is capable of forming a high-strength peptide gel may be obtained.

In the amino acid sequence, $c_1$ and $c_2$ each represent an acidic amino acid residue. An acidic amino acid is preferably aspartic acid or glutamic acid. This is because those amino acids are easily available. $c_1$ and $c_2$ may be the same amino acid residue or different amino acid residues.

In the amino acid sequence, d represents a hydrophobic amino acid residue. As described above, the self-assembling peptide has a hydrophobic amino acid residue as d and a given symmetric structure, thereby it is conceivable that the self-assembling peptide is capable of forming a gel more excellent in mechanical strength than a conventional peptide gel. Although the reason why such effect is exerted is not unclear, a possible reason is as described below. That is, it is estimated that the self-assembling peptide of the present invention is capable of forming an assembled state having high uniformity because the amino acid residue d at position 7 is a hydrophobic amino acid residue, which makes an overlap of peptide molecules constant in self-assembling.

d preferably represents an alanine residue, a valine residue, a leucine residue, or an isoleucine residue. In this case, amino acids on the hydrophilic plane side of a β-sheet structure formed by the self-assembling peptide may be non-complementary in side chain length to each other. However, the self-assembling peptide is capable of exhibiting an excellent self-assembling ability and is capable of forming a peptide gel excellent in mechanical strength than ever before. This is an effect different greatly from the conventional finding that amino acids on the hydrophilic plane side of a β-sheet structure are preferably complementary in side chain length to each other in order to obtain an electrostatic attractive force suitable for self-assembling. The term "complementary in side chain length" as used herein means that the sum of the numbers of atoms mainly involved in side chain lengths of a pair of amino acid residues (for example, a basic amino acid residue and an acidic amino acid residue) which exhibits an interaction is constant. For example, FIG. 1 is a schematic view for describing a distance between peptide molecules having amino acid residues non-complementary in side chain length to each other. As shown in FIG. 1, the sum (7) of the numbers of atoms which are mainly involved in side chain lengths of an alanine residue-arginine residue pair surrounded by a dotted line is smaller than the sum (9) of the numbers of atoms which are mainly involved in side chain lengths of an aspartic acid residue-arginine residue pair surrounded by a solid line.

The total sum of charges in a neutral pH environment of amino acid residues included in the self-assembling peptide is substantially +2. That is, in the self-assembling peptide, a positive charge and a negative charge derived from side chains of amino acid residues included in the peptide in a neutral pH environment are not cancelled. In addition, both of amino acid residues at the N-terminus and the C-terminus are basic amino acid residues. Thus, in the self-assembling peptide of the present invention, for example, not only an electrostatic attractive force but also an electrostatic repulsive force act on peptide molecules, a delicate balance between those forces is maintained, and hence the self-assembling peptide is substantially free of excessive association. Accordingly, it is estimated that the self-assembling peptide is capable of forming a stable gel without being precipitated in a neutral pH environment. It should be noted that the term "neutral pH environment" as used herein refers to a region having a pH of 6 to 8, preferably a pH of 6.5 to 7.5.

The charges of the self-assembling peptide at each pH may be counted in accordance with, for example, the Lehninger (Biochimie, 1979) method. The Lehninger method may be conducted with a usable program found, for example, on the website of EMBL WWW Gateway to Isoelectric Point Service (http://www.embl-heidelberg.de/cgi/pi-wrapper.pl).

An aqueous solution including the self-assembling peptide is capable of forming a peptide gel excellent in mechanical strength. In one embodiment, the self-assembling peptide aqueous solution (preferably 0.2 to 5 w/v %, more preferably 0.2 to 2 w/v %, particularly preferably 0.2 to 1 w/v %, most preferably 0.3 to 0.8 w/v %) is capable of forming a gel having an absolute value L (g/s) of an amount of change in load per unit time in an approximate straight line of values measured at the initial stage (from the start of compression to between 8 and 10 seconds) after the start of compression of preferably 0.03 g/s or more, more preferably 0.035 g/s or more, particularly preferably 0.04 g/s or more in a compression test carried out at a compression speed of 0.05 mm/s using a jig whose tip has a spherical shape with a diameter of 3.2 mm and a curvature radius of 1.6 mm under a temperature condition of 22° C. As described in examples later, the compression test may be carried out, for example, by using a viscoelasticity measurement apparatus (product number "RSA III" manufactured by TA Instruments) equipped with a jig made of stainless-steel (manufactured by TA Instruments).

A self-assembling peptide according to a preferred embodiment of the present invention is exemplified below.

```
n-RLDLRLALRLDLR-c    (SEQ ID NO: 1)

n-RLDLRLLLRLDLR-c    (SEQ ID NO: 2)

n-RADLRLALRLDLR-c    (SEQ ID NO: 6)

n-RLDLRLALRLDAR-c    (SEQ ID NO: 7)

n-RADLRLLLRLDLR-c    (SEQ ID NO: 8)

n-RADLRLLLRLDAR-c    (SEQ ID NO: 9)

n-RLDLRALLRLDLR-c    (SEQ ID NO: 10)

n-RLDLRLLARLDLR-c    (SEQ ID NO: 11)
```

The self-assembling peptide may be manufactured by any appropriate manufacturing method. Examples thereof include a chemical synthesis method such as a solid-phase method such as an Fmoc method or a liquid-phase method and a molecular biological method such as gene recombinant expression.

C. Modified Peptide

The modified peptide of the present invention includes the above-mentioned self-assembling peptide subjected to any appropriate modification as long as the self-assembling ability is maintained. A site at which the modification is carried out may be an N-terminal amino group of the self-assembling peptide, may be a C-terminal carboxyl group thereof, or may be both of the groups.

Any appropriate modification may be selected as the modification in such a range that the resultant modified peptide has a self-assembling ability. Examples of the modification include: introduction of a protective group such as acetylation of an N-terminal amino group or amidation of a C-terminal carboxyl group; introduction of a functional group such as alkylation, esterification, or halogenation; hydrogenation; introduction of a saccharide compound such as a monosaccharide, a disaccharide, an oligosaccharide, or a polysaccharide; introduction of a lipid compound such as a fatty acid, a phospholipid, or a glycolipid; introduction of an amino acid or a protein; introduction of DNA; and introduction of any other compound having a bioactivity or the like. When the amino acid or the protein is introduced, the peptide after the introduction is an added peptide in which any appropriate amino acid is added to the self-assembling peptide at the N-terminus and/or the C-terminus. In this description, the added peptide is also included in the modified peptide. The modifications may be performed alone or in combination. For example, the added peptide in which a desired amino acid has been introduced into the above-mentioned self-assembling peptide at the C-terminus may be acetylated at the N-terminus and amidated at the C-terminus.

The added peptide (modified peptide) does not have features of the above-mentioned self-assembling peptide as a whole in some cases. Specific examples thereof include a case where the addition of any appropriate amino acid makes a sequence in the N-terminal direction and a sequence in the C-terminal direction asymmetric with respect to a hydrophobic amino acid residue at position 7 in the center, and a case where a hydrophobic amino acid residue and a hydrophilic amino acid residue are included at an equal ratio. Even in such case, the self-assembling peptide has an extremely excellent self-assembling ability, and hence the added peptide obtained by adding any appropriate amino acid to the self-assembling peptide is also capable of forming a peptide gel excellent in mechanical strength.

When the amino acid or the protein is introduced, the number of amino acid residues that construct the modified peptide after the introduction is preferably 14 to 200, more preferably 14 to 100, more preferably 14 to 50, particularly preferably 14 to 30, most preferably 14 to 20. This is because when the number of amino acid residues exceeds 200, the self-assembling ability of the self-assembling peptide may be impaired.

The kind and position of the amino acid to be introduced may be appropriately set depending on applications of the modified peptide and the like. It is preferred that a hydrophobic amino acid and a hydrophilic amino acid be introduced alternately from an arginine residue (hydrophilic amino acid) at the N-terminus and/or the C-terminus of the self-assembling peptide.

Specific examples of the amino acid to be introduced include: REDV (SEQ ID NO: 14), EILDV (SEQ ID NO: 15), YEKPGSPPREVVPRPRPGV (SEQ ID NO: 16), KNNQKSEPLIGRK (SEQ ID NO: 17), YIGSR (SEQ ID NO: 18), RNIAELLKDI (SEQ ID NO: 19), RYVVLPRPVCFEKGMNYTVR (SEQ ID NO: 20), IKVAV (SEQ ID NO: 21), PDSGR (SEQ ID NO: 22), amino acid sequences including RGD sequences (for example, GRGDSPASS (SEQ ID NO: 23), RGDN (SEQ ID NO: 24), RGDF (SEQ ID NO: RGDT (SEQ ID NO: 26), RGDA (SEQ ID NO: 27), RGD, and RGDS (SEQ ID NO: M), and the like as cell adhesion factors; PPKKKRKV (SEQ ID NO: 29), PAAKRVKLD (SEQ ID NO: 30), PQPKKKP (SEQ ID NO: 31), QRKRQK (SEQ ID NO: 32), and the like as nuclear transport signals; MMSFVSLLLVGILFWATEAEQLTLCEVFQ (SEQ ID NO: and the like as endoplasmic reticulum transport signals; and MLSLRQSIRFFLPATRTLCSSRYLL (SEQ ID NO: 34) and the like as mitochondrial transport signals. Those sequences may be introduced alone or in combination. Further, the amino acid sequence to be introduced and the self-assembling peptide may be linked together via one or more of any appropriate amino acids.

The modification may be performed by any appropriate method depending on the kinds and the like.

An aqueous solution including the modified peptide is capable of forming a peptide gel excellent in mechanical strength. In one embodiment, a modified peptide aqueous solution (preferably 0.2 to 5 w/v %, more preferably 0.2 to 2 w/v %, particularly preferably 0.2 to 1 w/v %, most preferably 0.3 to 0.8 w/v %) is capable of forming a gel having an absolute value L (g/s) of an amount of change in load per unit time in an approximate straight line of values measured at the initial stage (from the start of compression to between 8 and 10 seconds) after the start of compression of preferably 0.03 g/s or more, more preferably 0.035 g/s or more, particularly preferably 0.04 g/s or more in a compression test carried out at a compression speed of 0.05 mm/s using a jig whose tip has a spherical shape with a diameter of 3.2 mm and a curvature radius of 1.6 mm under a temperature condition of 22° C.

D. Peptide Gel

The peptide gel of the present invention is formed from an aqueous solution including the self-assembling peptide and/or the modified peptide (hereinafter, "the self-assembling peptide and/or the modified peptide" are/is sometimes referred to as "the peptide of the present invention"). It is estimated that the peptide of the present invention assembles spontaneously in an aqueous solution, forms a fiber-like molecule assembly having a width at a nanometer scale, the so-called nanofibers, and forms a three dimensional network structure mainly owing to an electrostatic interaction acting on the nanofibers, and then forms a gel. The aqueous solution may include only one kind or two or more kinds of the peptide of the present invention. The aqueous solution may further include any appropriate additive in addition to the peptide of the present invention and water. Further, the aqueous solution may include insoluble matter such as a cell.

The concentration of the peptide of the present invention in the aqueous solution is preferably 0.2 to 5 w/v %, more preferably 0.2 to 2 w/v %, particularly preferably 0.2 to 1 w/v %, most preferably 0.3 to 0.8 w/v %. When the concentration falls within such a range, a peptide gel excellent in mechanical strength may be obtained. Further, when the peptide gel is used as a substrate for cell culture, a satisfactory cell survival rate may be provided.

The additive may be appropriately selected depending on applications of the peptide gel, kinds of the peptide included therein, and the like. Specific examples of the additive include: pH adjusters such as sodium hydroxide, potassium hydroxide, hydrochloric acid, phosphoric acid, sodium hydrogen carbonate, and sodium carbonate; amino acids; vitamins such as vitamin A, vitamin B family, vitamin C, vitamin D, vitamin E, and derivatives thereof; saccharides such as a monosaccharide, a disaccharide, and an oligosaccharide; polysaccharides such as hyaluronic acid, chitosan, and hydrophilic cellulose; alcohols such as ethanol, propanol, and isopropanol; polyhydric alcohols such as glycerin and propylene glycol; pigments such as phenol red; bioactive substances such as hormones, cytokines (including hemopoietic factors and growth factors), and peptides; enzymes; antibodies; DNA; RNA; and other general low-molecular compounds. The additives may be added alone or in combination. The concentration of the additive in the aqueous solution may be appropriately set depending on the purposes, applications of the peptide gel, and the like.

Specific examples of the aqueous solution including the additive include various buffers such as phosphate buffered saline (PBS) and Tris-HCl, a medium for cell culture such as a Dulbecco's modified Eagle medium (DMEM), and an aqueous solution having a pH adjusted with sodium hydroxide, hydrochloric acid, sodium hydrogen carbonate, or the like.

The aqueous solution may have any appropriate pH depending on the purposes. For example, the aqueous solutions before and after dissolving the peptide of the present invention each have a pH of preferably 5 to 9, more preferably 5.5 to 8, particularly preferably 6.0 to 7.5. When the pH falls within such a range, a peptide gel excellent in mechanical strength may be obtained. In addition, a satisfactory cell survival rate may be obtained when the aqueous solution includes a cell. Further, when the pH falls within such a range, peptide degradation hardly occurs under a high-temperature and pressurized condition, and hence the peptide gel may be subjected to high-pressure steam sterilization treatment such as autoclaving. As a result, a peptide gel in a sterile state may be obtained in a simple manner.

Any appropriate cell may be selected as the cell depending on the purposes and the like. The cell may be an animal cell or a plant cell. Specific examples of the cell include cartilage cells, myoblasts, bone marrow cells, fibroblasts, hepatocytes, and cardiomyocytes.

The peptide gel of the present invention has an absolute value L (g/s) of an amount of change in load per unit time of preferably 0.03 g/s or more, more preferably 0.035 g/s or more, particularly preferably 0.04 g/s or more in an approximate straight line of values measured at the initial stage (from the start of compression to between 8 and 10 seconds) after the start of compression in a compression test carried out at a compression speed of 0.05 mm/s using a jig whose tip has a spherical shape with a diameter of 3.2 mm and a curvature radius of 1.6 mm under a temperature condition of 22° C. The peptide gel with such mechanical strength may be formed, for example, from an aqueous solution including the peptide of the present invention at a concentration of preferably 0.2 to 5 w/v %, more preferably 0.2 to 2 w/v %, particularly preferably 0.2 to 1 w/v %, most preferably 0.3 to 0.8 w/v %.

The peptide gel of the present invention has a visible light transmittance, which is measured at an absorbance of 380 nm to 780 nm in a cell having an optical path length of 10 mm, of preferably 50% or more, more preferably 70% or more, particularly preferably 90% or more. The peptide gel having such visible light transmittance may be formed, for example, from an aqueous solution including the peptide of the present invention at concentration of 0.2 to 2 w/v %. Further, a reduction rate in visible light transmittance (%) after the peptide gel has been left to stand in a sealed state at room temperature for a long period of time (for example, 2 months) (100−(visible light transmittance after storage/visible light transmittance before storage×100)) is preferably 30% or less, more preferably 20% or less, particularly preferably 10% or less. The peptide gel having such high visible light transmittance has advantages such as facilitating cell observation with a fluorescent light microscope or the like when used as a substrate for cell culture. The visible light transmittance may be measured, for example, by using a UV/VIS measurement apparatus.

The peptide gel may be formed by any appropriate method. Typically, the peptide gel may be formed by leaving an aqueous solution including at least one kind of the peptide of the present invention to stand still. The temperature or time in leaving the aqueous solution to stand still is not particularly limited as long as the peptide of the present invention self-assembles to form a gel, and may be appropriately set depending on use purposes of the gel, kinds of the peptide, concentrations, and the like. The time for leaving the aqueous solution to stand still is generally 1 minute or more, preferably 3 minutes or more, more preferably 5 minutes or more. The temperature is generally 4 to 50° C., preferably 15 to 45° C.

E. Applications of Self-Assembling Peptide, Modified Peptide, and Peptide Gel Preferred applications of the self-assembling peptide, modified peptide, and peptide gel of the present invention include, for example: substrates for cell culture; cosmetics such as skin care products and hair care products; medical products such as decubitus preparations, bone fillers, injectable agents for aesthetic, adjuvant to ophthalmic operation, artificial vitreous bodies, artificial lenses, joint lubricants, ophthalmic solutions, DDS substrates, and hemostats; water retention materials for moistening; desiccants; and coating agents for medical devices such as contact lenses.

F. Substrate for Cell Culture

The substrate for cell culture of the present invention includes at least one selected from the self-assembling peptide, the modified peptide, and the peptide gel described above. The substrate for cell culture of the present invention is formed from a self-assembling peptide and/or a modified peptide obtained by chemical synthesis. Hence, there is no risk of contamination with a pathogen and the like and cell culture may be carried out safely. Further, the gel formed from the peptide of the present invention may be transparent in a neutral pH environment and excellent in mechanical strength, and hence the substrate for cell culture of the present invention is excellent in visibility and handleability during cell culture.

In the interior of the substrate for cell culture, the peptides of the present invention self-assemble, form into fibers, and form a three dimensional network structure. Thus, not only culture on the substrate for cell culture but also culture in the substrate for cell culture may be carried out.

When culture is carried out on the substrate for cell culture, cells to be cultured may be placed and cultured on the preformed peptide gel including the peptide of the present invention. When culture is carried out in the substrate for cell culture, the peptide of the present invention or the peptide aqueous solution is mixed with cells or a cell suspension, and a peptide gel may be formed from the mixture to culture the cells.

A liquid phase of the peptide gel may be replaced by a desired culture solution through solvent replacement. The solvent replacement may be carried out, for example, by using a trade name "Cell Culture Insert" or the like. The details about the peptide gel (for example, peptide concentration, kind of an additive which may be included in an aqueous solution (mixture), and pH) and a forming method therefor are as described in the section D.

Any appropriate cell may be selected as the cell to be cultured depending on the purposes and the like. The cell may be an animal cell or a plant cell. Specific examples of the cell include cartilage cells, myoblasts, bone marrow cells, fibroblasts, hepatocytes, and cardiomyocytes. A culture solution and a culture condition may be appropriately selected depending on kinds of cells to be cultured, purposes, and the like.

The substrate for cell culture of the present invention is excellent in biocompatibility and safety, and hence may be suitably utilized, for example, in three dimensional cell culture in the regenerative medicine field or the like.

G. Manufacturing method for Sterile Peptide

A manufacturing method for a sterile peptide of the present invention includes the step of sterilizing the self-assembling peptide and/or the modified peptide under a pressurized condition at 100° C. or more. Those peptides are typically subjected to sterilization treatment in the form of a peptide aqueous solution or a peptide gel formed from the peptide aqueous solution. The peptide aqueous solution has a pH of preferably 5 to 9, more preferably 5.5 to 8, particularly preferably 6.0 to 7.5. When the peptide aqueous solution has such pH, peptide degradation does not substantially occur even in sterilization under a temperature condition of 100° C. or more, and hence the peptide of the present invention in a sterile state may be obtained. The peptide aqueous solution and the peptide gel are as described in the section D.

Any appropriate sterilization method may be adopted as the sterilization method. For example, a high-temperature and high-pressure saturated water vapor sterilization (so-called autoclave sterilization) method may be preferably employed. The pressure during the autoclave sterilization is preferably 0.122 to 0.255 MPa, more preferably 0.152 to 0.233 MPa. Further, the sterilization temperature is preferably 105 to 135° C., more preferably 110 to 125° C. Further, the sterilization time is preferably 1 to 60 minutes, more preferably 3 to 40 minutes, particularly preferably 5 to 30 minutes.

The autoclave sterilization may be performed using a commercially available autoclave apparatus.

H. Manufacturing Method for Article Coated with Peptide Gel

A manufacturing method for an article coated with a peptide gel of the present invention includes the steps of: freezing the peptide gel (freezing step); melting the frozen peptide gel to provide a peptide sol (melting step); coating at least part of a surface of an article to be coated with the peptide sol (coating step); and reconstructing a peptide gel from the peptide sol (gelling step). The method may further include any appropriate step as necessary. When the peptide gel of the present invention is frozen and melted, a bond between peptide molecules is cleaved, and hence a three dimensional network structure that constructs the gel collapses. Thus, a sol having peptide molecules uniformly dispersed in an aqueous solution may be obtained. At least part of the surface of an article to be coated is coated with the sol with high uniformity and the sol is then turned into a gel. Thus, the surface of the article may be uniformly coated with the peptide gel.

H-1. Freezing Step

Any appropriate condition may be adopted as a freezing condition as long as the peptide gel is frozen. A freezing temperature has only to be equal to or less than a temperature at which the peptide gel is frozen. A freezing speed is also not limited, and the peptide gel may be gradually frozen or quickly frozen. For example, the peptide gel may be suitably frozen by placing the peptide gel under a temperature condition of −10° C. or less.

Any appropriate freezing means may be selected as freezing means, such as a household or industrial freezer or liquid nitrogen. It should be noted that the frozen peptide gel may be preserved in a frozen state for any appropriate period of time before the melting step.

When the peptide gel to be frozen is a gel formed from a peptide aqueous solution including an additive, the concentration of the additive is preferably such a concentration that does not adversely affect gel reconstruction in the gelling step. The concentration may be appropriately set depending on the kinds, concentrations, and the like of the peptide. In general, however, a low concentration is preferred. For example, in the case of HEPES and a Tris-HCl solution, the final concentration is preferably 50 mM or less, more preferably 40 mM or less. In the case of a sodium hydrogen carbonate solution and a sodium carbonate solution, the final concentration is preferably 5 mM or less, more preferably 4 mM or less. In the case of a PBS solution, the final concentration is preferably 0.5×PBS or less, more preferably 0.3× PBS or less. Further, in the case of Pharmacopoeia physiological saline, the final concentration is preferably 0.5 wt % or less, more preferably 0.4 wt % or less.

H-2. Melting Step

A melting temperature may be set to any appropriate temperature as long as it is a temperature at which the frozen peptide gel obtained in the freezing step is melted to form a sol. The frozen peptide gel may be melted at a constant temperature, or may be melted at different temperatures in a stepwise manner. A melting speed and time is not limited, and the frozen peptide gel may be gradually melted or quickly melted. The frozen peptide gel may suitably melted, for example, by placing the frozen peptide gel under a temperature condition of 5 to 70° C., preferably 15 to 45° C.

Any appropriate means may be selected as melting means. Specific examples of the melting means include a water bath, an oil bath, and a thermostat bath.

When the peptide gel is frozen and melted as described above, a variety of bonds between peptide molecules that form the gel are cleaved to yield a sol. The sol obtained by freezing and melting has a remarkably reduced viscosity because a variety of bonds between peptide molecules have been sufficiently cleaved, and hence is capable of uniformly coating the surface of an article to be coated without difficulty. It should be noted that, from the viewpoint of providing higher uniformity of the sol, the frozen peptide gel may be melted while vibrated to such an extent that air bubbles are not generated in the resultant sol, or the sol obtained by melting may be vibrated and then subjected to the coating step. Examples of such vibration method include shaking the frozen peptide gel or sol and applying ultrasound thereto.

H-3. Coating Step

Any appropriate method may be adopted as a coating method. Specific examples thereof include a dispenser coating mode, an immersion mode, a bar coater mode, a mode including applying a sol onto the surface of an article to be coated with a centrifugal force, and a mode including applying a sol fluidized by tilting an article to be coated onto the surface thereof. In the sol, a variety of bonds between peptide molecules are sufficiently cleaved to reduce its viscosity remarkably, and peptide molecules are sufficiently dispersed. Thus, the sol is capable of forming a uniform layer on the surface of an article to be coated.

Any appropriate article may be adopted as the article to be coated. Examples thereof include a container such as a tube or a bottle, a cell culture instrument such as a multi-well dish or a laboratory dish, and a plate such as a slide glass. The article to be coated is formed of any appropriate material such as glass, plastic, or metal.

H-4. Gelling Step

A Condition for reconstructing a gel (temperature, time, or the like) is not limited as long as a peptide gel is reconstructed, and may be appropriately set depending on kinds, concentrations, and the like of the peptide. The peptide of the present invention has a self-assembling ability and hence is capable of self-assembling and reconstructing a gel spontaneously by setting the condition to an appropriate condition.

As the condition for reconstructing a gel, for example, it is sufficient to reconstruct a gel that an article whose surface is coated with the peptide sol is left to stand still. A temperature in leaving the article to stand still is preferably 15° C. or more, more preferably 25 to 45° C. A time in leaving the article to stand still is preferably 1 minute or more, more preferably 5 minutes or more.

The thickness of the peptide gel reconstructed in the gelling step, that is, the thickness of a coating film on an article surface may be, for example, 1 μm or more, preferably 1 μm to 1 cm.

EXAMPLES

Hereinafter, the present invention is specifically described by way of examples. However, the present invention is by no means limited by these examples.

Example 1

A self-assembling peptide formed of an amino acid sequence of SEQ ID NO: 1 described in Table 1 was synthesized by an Fmoc solid-phase synthesis method. Next, the self-assembling peptide was acetylated at the N-terminus and amidated at the C-terminus by a conventional method to afford a modified peptide 1 ([CH$_3$CO]-RLDLRLALRLDLR-[NH$_2$] (SEQ ID NO: 35)).

The resultant modified peptide 1 was dissolved in a 0.1 wt % sodium hydrogen carbonate solution at concentrations of 0.2, 0.4, and 0.6 w/v % to afford peptide solutions. The resultant peptide solutions were each measured for a pH value using pH test paper (trade name: pH Indicator Papers, manufactured by Whatman International Ltd., measurement range pH=6.0 to 8.1, Cat. No. 2629 990), and the pH was found to fall within the range of 6.9 to 7.8. 300 μl each of the peptide solutions were charged into a trade name "Nunc Tissue Culture Inserts" (membrane diameter: 10 mm, pore size: 8.0 μm, membrane material: polycarbonate) (product number "Cat. No: 136862" manufactured by Nalge Nunc International) and left to stand still at 22° C. for 2 hours to form gels. The gels each had a thickness of approximately 2 mm. The resultant gels were subjected to solvent replacement with DMEM for 12 hours to afford peptide gels 1 (liquid phase: DMEM) at peptide concentrations of 0.2, 0.4, and 0.6 w/v %. The resultant peptide gels 1 at the respective concentrations were subjected to the following compression test to measure mechanical strength.

[Compression Test]

The mechanical strength was measured by compressing each gel at a speed of 0.05 mm/s (s=second) using a viscoelasticity measurement apparatus (product number "RSA III" manufactured by TA Instruments) equipped with a jig made of stainless-steel whose tip has a spherical shape (diameter: 3.2 mm, curvature radius: 1.6 mm) (manufactured by TA Instruments) under a condition of 22° C.

Figure 2:
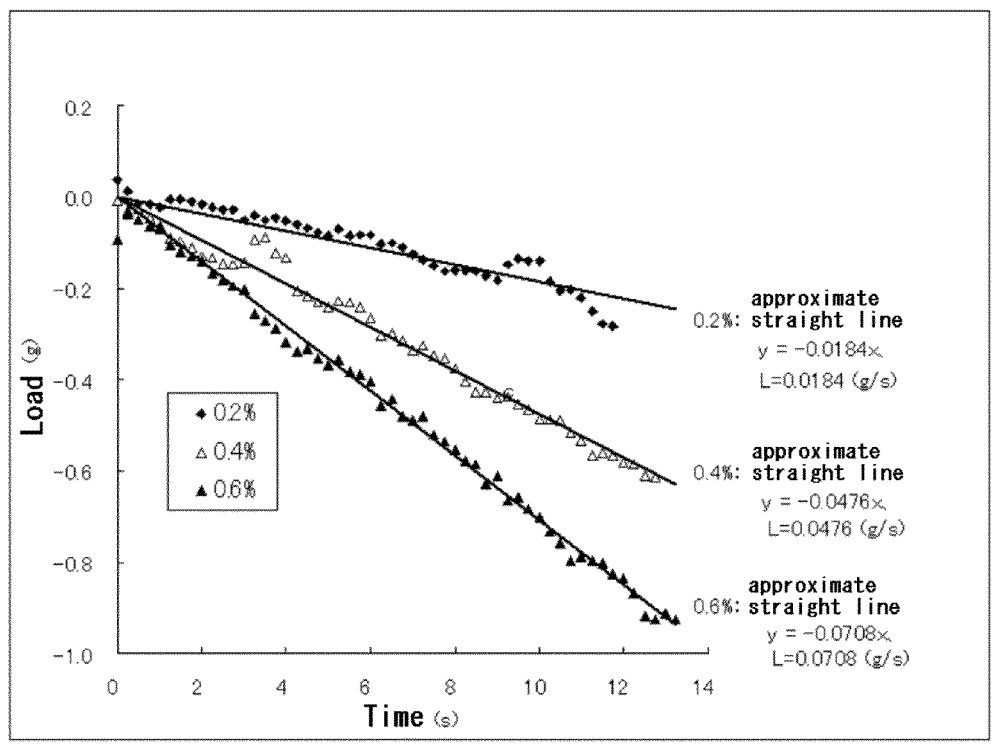
FIG. 2 is a graph showing the results of a compression test on a peptide gel of Example 1.

FIG. 2 shows the results of the compression test. FIG. 2 shows a relationship between a load applied to the apparatus in gradually compressing a sample with the jig and a time, and a larger slope of an approximate straight line indicates higher mechanical strength. Thus, when the absolute value of a slope of an approximate straight line of values measured at the initial stage (from the start of compression to between 8 and 10 seconds) after the start of compression (amount of change in load per unit time) is defined as L, a larger L value indicates higher mechanical strength. As shown in FIG. 2, the peptide gel 1 at 0.4 w/v % had an absolute value L of an amount of change in load per unit time of 0.0476 g/s, which was determined for about 10 seconds after the start of compression in the compression test.

The peptide gel 1 at 0.4 w/v % was grasped with tweezers and transported. As a result, as shown in FIG. 3(a), the peptide gel 1 had sufficient strength to grasp and was excellent in handleability.

Example 2

A modified peptide 2 ([CH$_3$CO]-RLDLRLLLRLDLR-[NH$_2$] (SEQ ID NO: 36)) was obtained in the same manner as in Example 1 except that an amino acid sequence of SEQ ID NO: 2 was adopted in place of the amino acid sequence of SEQ ID NO: 1. Peptide gels 2 (liquid phase: DMEM) at peptide concentrations of 0.2, 0.4, and 0.6 w/v % were formed in the same manner as in Example 1 except that the modified peptide 2 was used in place of the modified peptide 1.

Figure 4:
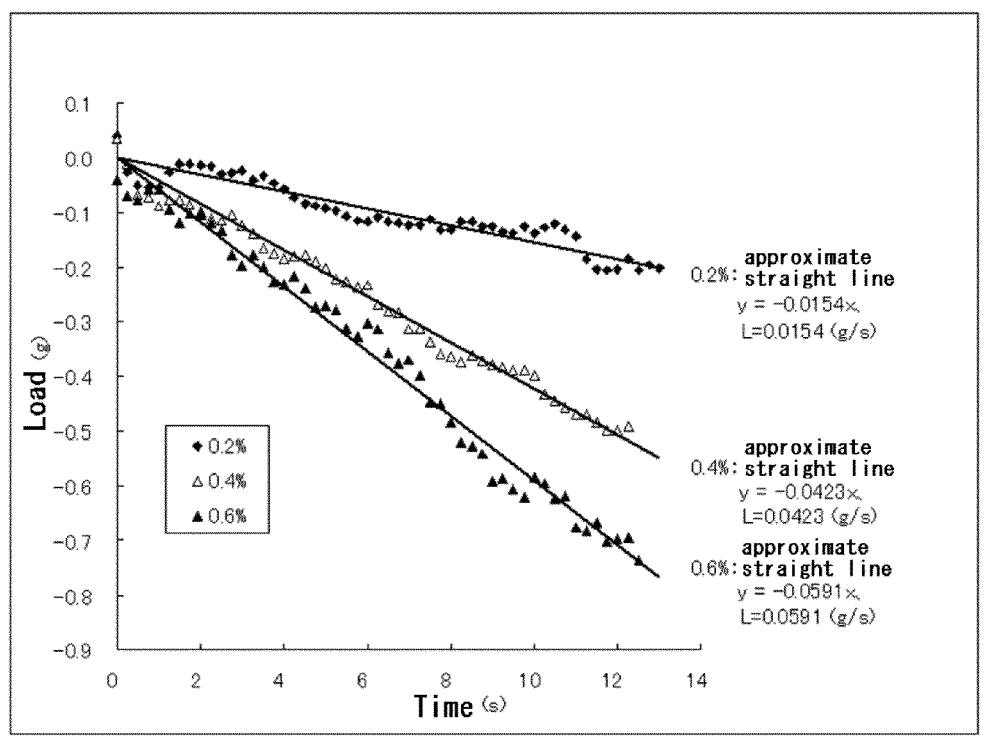
FIG. 4 is a graph showing the results of a compression test on a peptide gel of Example 2.

The resultant peptide gels were each measured for mechanical strength in the same manner as in Example 1. FIG. 4 shows the results. As shown in FIG. 4, the peptide gel 2 at 0.4 w/v % had an absolute value L of an amount of change in load per unit time of 0.0423 g/s in the compression test.

The peptide gel 2 at 0.4 w/v % was grasped with tweezers and transported. As a result, as shown in FIG. 3(b), the peptide gel 2 had sufficient strength to grasp and was excellent in handleability.

Example 3

A modified peptide 3 ([CH$_3$CO]-RLDLRLALRLDLRL-[NH$_2$] (SEQ ID NO: 37)) was obtained in the same manner as in Example 1 except that an amino acid sequence of SEQ ID NO: 3 was adopted in place of the amino acid sequence of SEQ ID NO: 1. Peptide gels 3 (liquid phase: DMEM) at peptide concentrations of 0.2 and 0.4 w/v % were formed in the same manner as in Example 1 except that the modified peptide 3 was used in place of the modified peptide 1.

Figure 5:
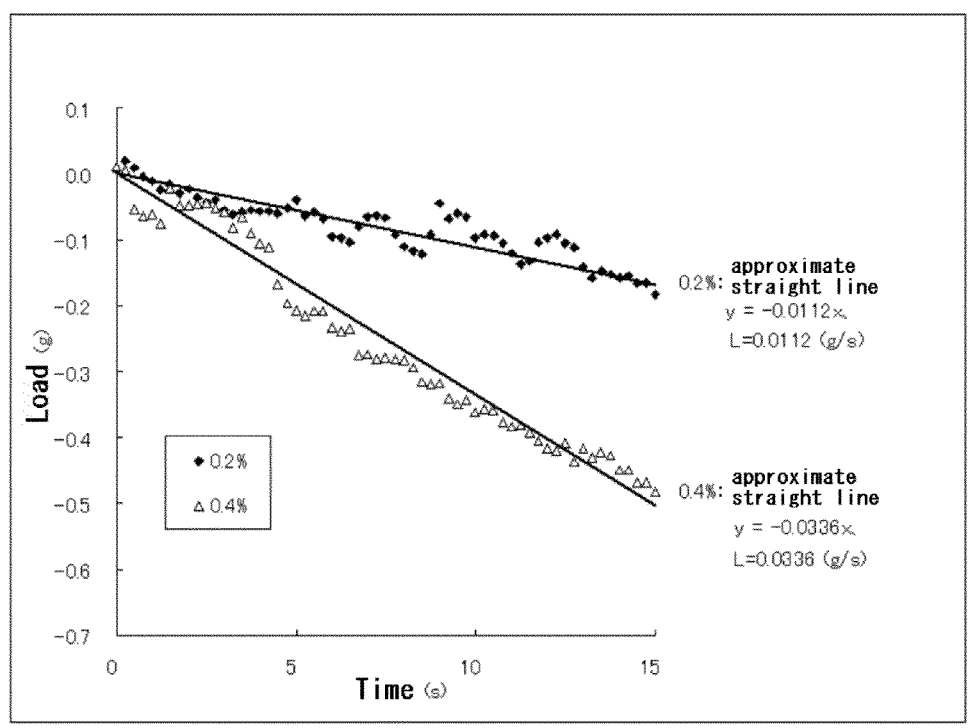
FIG. 5 is a graph showing the results of a compression test on a peptide gel of Example 3.

The resultant peptide gels were each measured for mechanical strength in the same manner as in Example 1. FIG. 5 shows the results. As shown in FIG. 5, the peptide gel 3 at 0.4 w/v % had an absolute value L of an amount of change in load per unit time of 0.0336 g/s in the compression test.

Comparative Example 1

A modified peptide c1 ([CH$_3$CO]-RASARADARA-DARASA-[NH$_2$] (SEQ ID NO: 38) was obtained in the same manner as in Example 1 except that an amino acid sequence of SEQ ID NO: 4 was adopted in place of the amino acid sequence of SEQ ID NO: 1. Peptide gels c1 (liquid phase: DMEM) at peptide concentrations of 0.2, 0.4, and 0.6 w/v % were formed in the same manner as in Example 1 except that the modified peptide c1 was used in place of the modified peptide 1.

Figure 6:
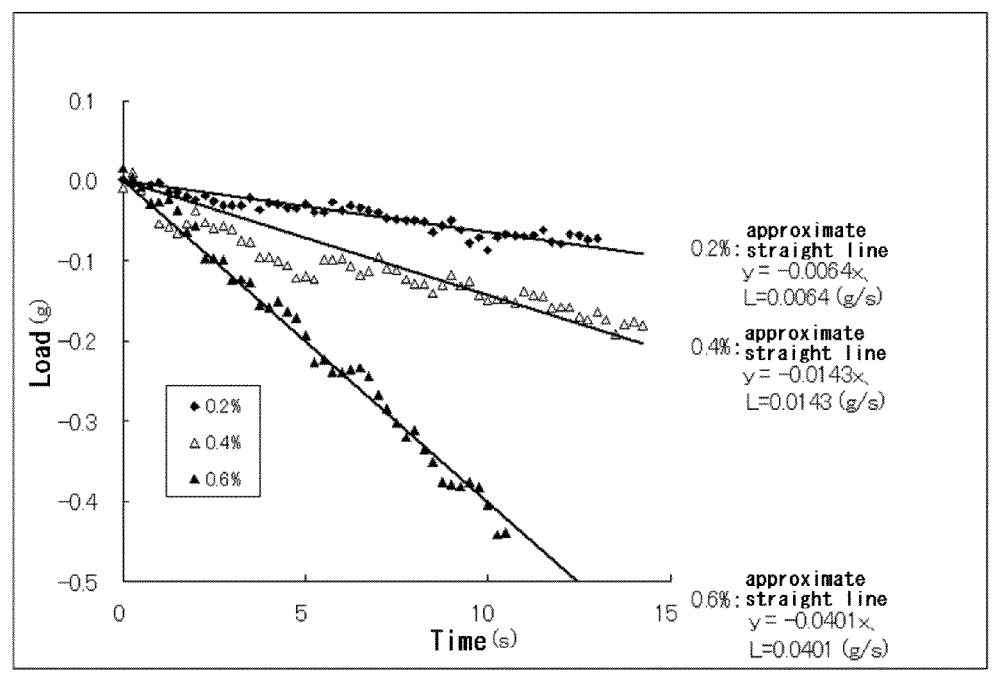
FIG. 6 is a graph showing the results of a compression test on a peptide gel of Comparative Example 1.

The resultant peptide gels were each measured for mechanical strength in the same manner as in Example 1. FIG. 6 shows the results. As shown in FIG. 6, the peptide gel c1 at 0.4 w/v % had an absolute value L of an amount of change in load per unit time of 0.0143 g/s in the compression test.

The peptide gel c1 at 0.4 w/v % was grasped with tweezers and transported. As a result, as shown in FIG. 3(c), the peptide gel c1 had insufficient mechanical strength and was problematic in handleability.

Comparative Example 2

A modified peptide c2 ([CH$_3$CO]-RASARADARASA-RADA-[NH$_2$] (SEQ ID NO: 39) was obtained in the same manner as in Example 1 except that an amino acid sequence of SEQ ID NO: 5 was adopted in place of the amino acid sequence of SEQ ID NO: 1. Peptide gels c2 (liquid phase: DMEM) at peptide concentrations of 0.2 and 0.4 w/v % were formed in the same manner as in Example 1 except that the modified peptide c2 was used in place of the modified peptide 1.

Figure 7:
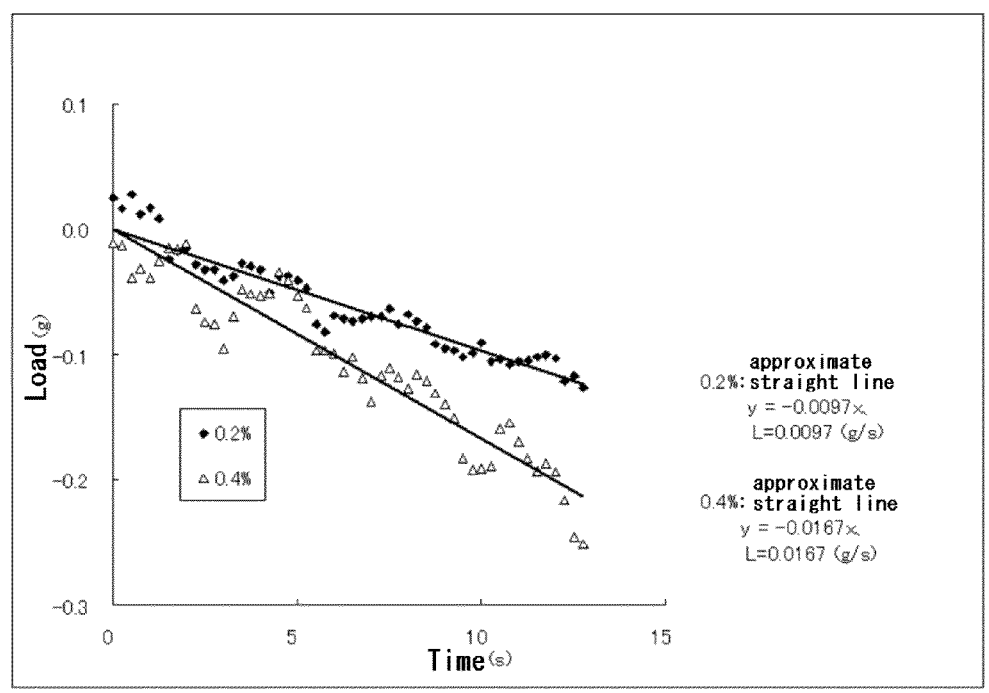
FIG. 7 is a graph showing the results of a compression test on a peptide gel of Comparative Example 2.

The resultant peptide gels were each measured for mechanical strength in the same manner as in Example 1. FIG. 7 shows the results. As shown in FIG. 7, the peptide gel c2 at 0.4 w/v % had an absolute value L of an amount of change in load per unit time of 0.0167 g/s in the compression test.

Example 4

A modified peptide 4 ([CH$_3$CO]-RGDNRLDLRLAL-RLDLR-[NH$_2$] (SEQ ID NO: 40)) was obtained in the same manner as in Example 1 except that an amino acid sequence of SEQ ID NO: 12 was adopted in place of the amino acid sequence of SEQ ID NO: 1. Peptide gels 4 (liquid phase: DMEM) at peptide concentrations of 0.2, 0.4, and 0.6 w/v % were formed in the same manner as in Example 1 except that the modified peptide 4 was used in place of the modified peptide 1.

Figure 8:
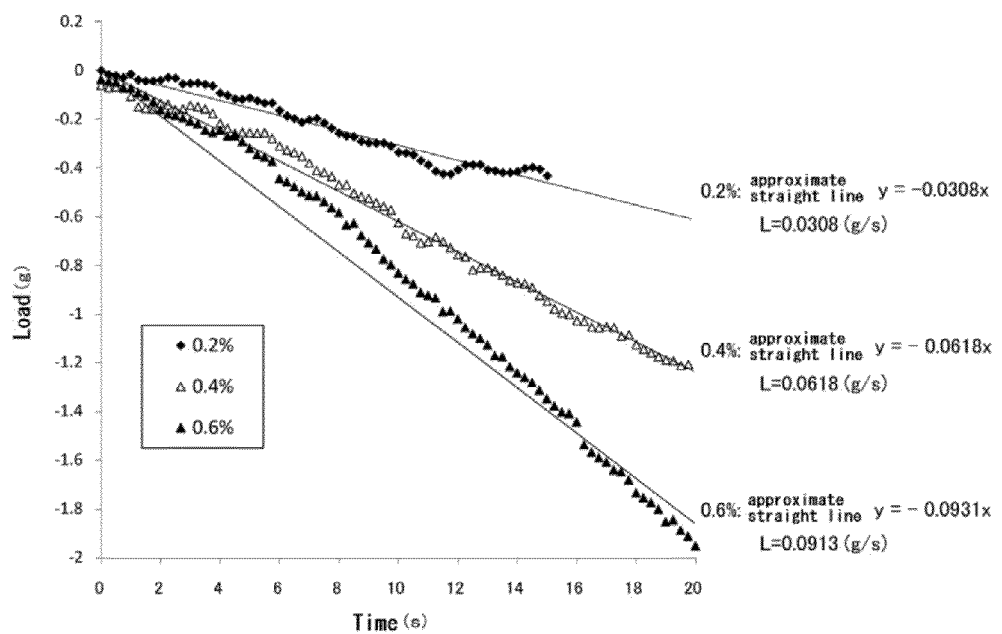
FIG. 8 is a graph showing the results of a compression test on a peptide gel of Example 4.

The resultant peptide gels were each measured for mechanical strength in the same manner as in Example 1. FIG. 8 shows the results. As shown in FIG. 8, the peptide gel 4 at 0.4 w/v % had an absolute value L of an amount of change in load per unit time of 0.0618 g/s in the compression test.

TABLE 1

| | Amino acid sequence | |
|---|---|---|
| Example 1 | n-RLDLRLALRLDLR-c | SEQ ID No: 1 |
| Example 2 | n-RLDLRLLLRLDLR-c | SEQ ID No: 2 |
| Example 3 | n-RLDLRLALRLDLRL-c | SEQ ID No: 3 |
| Example 4 | n-RGDNRLDLRLALRLDLR-c | SEQ ID No: 12 |
| Comparative Example 1 | n-RASARADARADARASA-c | SEQ ID No: 4 |
| Comparative Example 2 | n-RASARADARASARADA-c | SEQ ID No: 5 |

Figure 3:
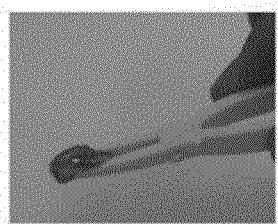
FIG. 3(a) is a photograph of a peptide gel of Example 1 grasped with tweezers.
FIG. 3(b) is a photograph of a peptide gel of Example 2 grasped with tweezers.
FIG. 3(c) is a photograph of a peptide gel of Comparative Example 1 grasped with tweezers.
Figure 3:
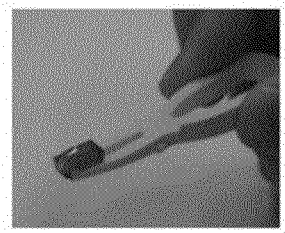
Figure 3:
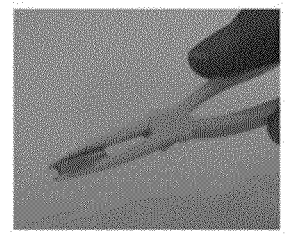

As shown in FIGS. 2 and 4 to 8, it is understood that the peptide of the present invention is capable of forming a peptide gel with high mechanical strength as compared to the self-assembling peptide of each of the comparative examples. Further, as shown in FIG. 3, it is understood that the peptide gel of the present invention has high mechanical strength and hence is extremely excellent in handleability. In addition, the peptide of the present invention is capable of forming a peptide gel with sufficient mechanical strength at a low peptide concentration and hence is advantageous in terms of cost as well.

Example 5

A cell suspension including mouse myoblasts (L6) at a cell concentration of $2.0 \times 10^6$ cells/ml and a peptide aqueous solution including the modified peptide 1 at 1.0 w/v % were mixed with each other at a volume ratio of 3:2 (cell suspension: peptide aqueous solution). The resultant mixture (cell concentration: $1.2 \times 10^6$ cells/ml, peptide concentration: 0.4 w/v %) was charged into a Cell Culture Insert (product number "353096" manufactured by BD Falcon) and left to stand still at room temperature for approximately 1 minute to form a peptide gel. The gel in the Cell Culture Insert was directly set in wells of a 24-well plate for tissue culture (product number "3820-024" manufactured by AGC TECHNO GLASS CO., LTD.) with 1 mL of a DMEM medium containing 10% calf serum. Next, cell culture was carried out in an incubator at 37° C. in the presence of 5% $CO_2$. Medium exchange was carried out only once on Day 2 after the start of culture. The gel was collected on Days 1, 2, and 4 after the start of culture, and DNA quantification was carried out using a trade name "CyQUANT (registered trademark) Cell Proliferation Assay Kit*for cells in culture**1000 assays*" (product number "C7026" manufactured by Invitrogen), to thereby calculate cell growth rates. The cell growth rates on Days 1, 2, and 4 after the start of culture were 150%, 180%, and 310%, respectively, when the cell growth rate immediately after the start of culture was defined as 100%, that is, the number of cells increased in accordance with a lapse of days (an average of n=3 was used for the calculation results).

Example 6

Cell culture and DNA quantification were carried out in the same manner as in Example 5 except that the modified peptide 2 was used in place of the modified peptide 1. As a result of calculation of cell growth rates, the cell growth rates on Days 1, 2, and 4 after the start of culture were 140%, 160%, and 250%, respectively, when the cell growth rate immediately after the start of culture was defined as 100%, that is, the number of cells increased in accordance with a lapse of days (an average of n=3 was used for the calculation results).

Example 7

Figure 9:
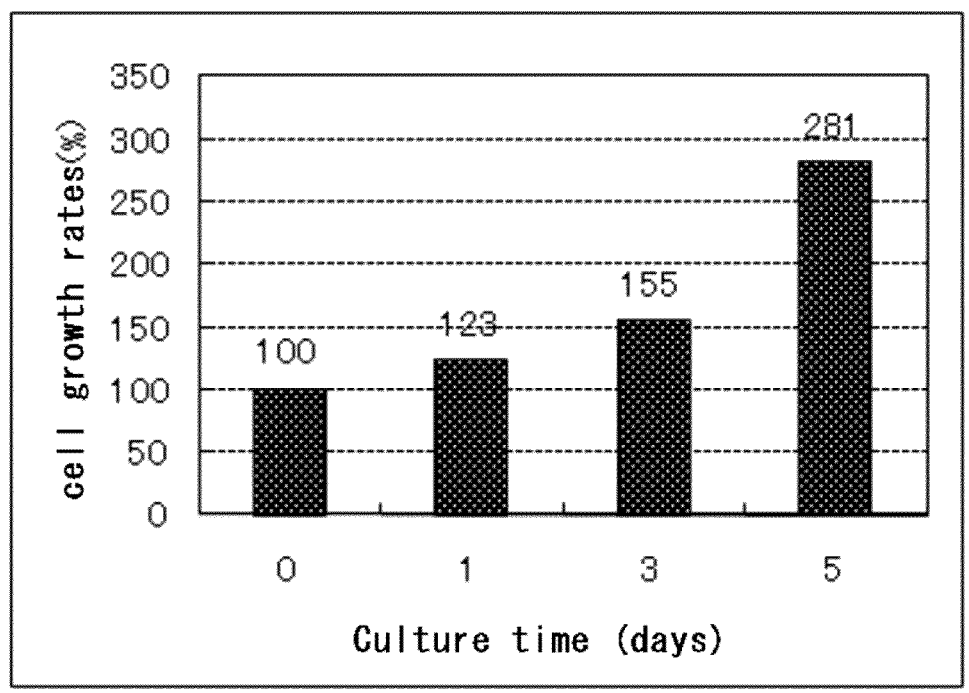
FIG. 9 is a graph showing cell growth rates in Example 7.

The modified peptide 1 was dissolved in a sodium carbonate solution to prepare a 0.5 w/v % peptide aqueous solution (final concentration of sodium carbonate: 2.75 mM). The peptide aqueous solution was subjected to sterilization treatment at 121° C. for 20 minutes using an autoclave apparatus (product number "MLS 3020" manufactured by SANYO Electric Co., Ltd.) to afford a peptide gel. The gel and a cell suspension obtained by suspending mouse NIH3T3 cells in a DMEM medium were uniformly mixed with each other at a volume ratio of 2:1 (gel:cell suspension) by pipetting. 100 µL of the resultant cell-gel mixture was added to each of five Cell Culture Inserts (product number "353096" manufactured by BD Falcon), and the Cell Culture Inserts were set in wells of a 24-well plate for tissue culture (product number "3820-024" manufactured by AGC TECHNO GLASS CO., LTD.) with 1 mL of a DMEM medium containing 10% calf serum. In this case, the cell concentration in the cell-gel mixture was $1.45 \times 10^5$ cells/100 µL. Next, cell culture was carried out in an incubator at 37° C. in the presence of 5% $CO_2$. Cell growth rates were measured using a trade name "Cell Counting Kit 8" (manufactured by DOJINDO LABORATORIES) on Day 0 (Hour 2), Day 1, Day 3, and Day 5 after the start of culture. As a result, as shown in FIG. 9, the cell growth rates increased in accordance with a lapse of culture days.

A specific procedure for the measurement of the cell growth rates described above is as described below. In other words, 1 mL of the medium in the well was exchanged by 1 mL of a fresh medium, 100 µL of a Cell Counting Kit 8 solution were added, and the Cell Culture Insert was set in the well, followed by incubation at 37° C. for 2 hours. After the incubation, 100 µL of the medium permeating the gel in the Cell Culture Insert were transferred to a well of a 96-well plate, and the absorbance of the medium at 450 nm was measured using a plate reader. Cell growth rates in the respective culture days were determined with the absorbance of a sample on Day 0 after the start of culture defined as 100.

As seen from the results of Examples 5 to 7, the peptide gel of the present invention has biocompatibility and hence may be suitably used as a substrate for cell culture.

Example 8

The modified peptide 1 was dissolved in a sodium carbonate solution to prepare a 0.5 w/v % peptide aqueous solution (final concentration of sodium carbonate: 4.5 mM). The peptide aqueous solution had a pH in a neutral region. The peptide aqueous solution was subjected to sterilization treatment at 121° C. for 20 minutes using an autoclave apparatus (product number "MLS 3020" manufactured by SANYO Electric Co., Ltd.). The mass of a peptide molecule included in the peptide aqueous solution before or after the sterilization treatment was examined by a matrix-assisted laser desorption/ionization time-of-flight mass spectrometry method (MALDI-TOF-MS) using a time-of-flight mass spectrometry apparatus (product number "autoflex III" manufactured by Bruker). FIG. 10 show the results.

Comparative Example 3

Sterilization treatment and mass spectrometry (MALDI-TOF-MS) were carried out in the same manner as in Example 8 except that a trade name "PuraMatrix™" (manufactured by 3-D Matrix, Ltd.) was used in place of the peptide aqueous solution of the modified peptide 1. FIG. 11 show the results.

As shown in FIG. 10, the peptide of the present invention is substantially free of degradation by the sterilization treatment. Thus, the peptide of the present invention may be turned into a sterile state through the sterilization treatment. Meanwhile, as shown in FIG. 11, it is understood that the trade name "PuraMatrix™" (manufactured by 3-D Matrix, Ltd.) undergoes peptide degradation through the sterilization treatment. This is presumably because the trade name "PuraMatrix™" (manufactured by 3-D Matrix, Ltd.) is an acidic peptide aqueous solution.

Example 9

Figure 12A:
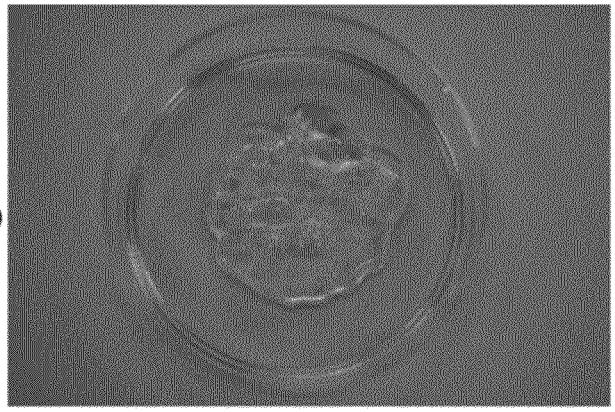
FIGS. 12(a), 12(b), and 12(c) are a photograph of a gel transferred to a laboratory dish, a photograph of a frozen gel, and a photograph of a laboratory dish whose entire surface is uniformly coated with a peptide gel, respectively.
Figure 12B:
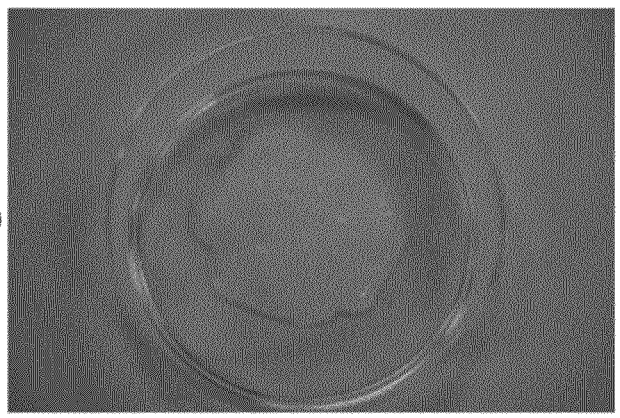
Figure 12C:
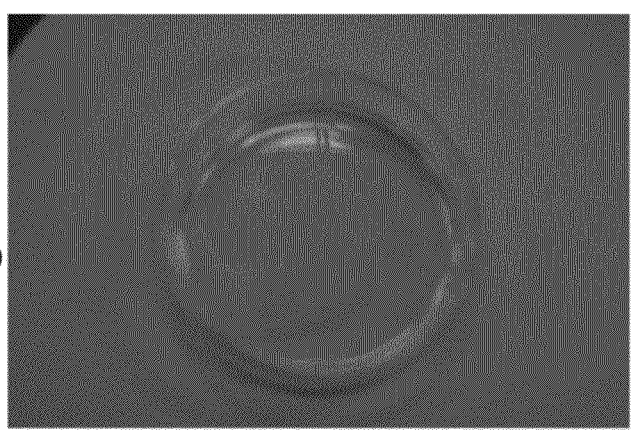

The modified peptide 1 was dissolved in a sodium carbonate solution to prepare a 0.8 w/v % peptide aqueous solution (final concentration of sodium carbonate: 4.5 mM). The resultant peptide aqueous solution was left to stand still at 22° C. for 2 hours to form a peptide gel. The gel was transferred to a laboratory dish (diameter: 6 cm) made of glass without any particular care. FIG. 12(*a*) shows a photograph in this case. As shown in FIG. 12(*a*), the gel included air bubbles and was too hard to uniformly coat the laboratory dish.

The laboratory dish with the gel was placed in a freezer at −20° C. to freeze the gel. FIG. 12(*b*) shows a photograph of the frozen gel. After that, the laboratory dish was taken out of the freezer, and the gel was melted under a room temperature condition while the laboratory dish was shaken. The resultant sol was applied to the entire bottom of the laboratory dish. The laboratory dish was left to stand still in this state to reconstruct the gel. Thus, the laboratory dish whose entire bottom was uniformly coated with the peptide gel was obtained. FIG. 12(*c*) shows a photograph of the laboratory dish.

Example 10

Figure 13A:
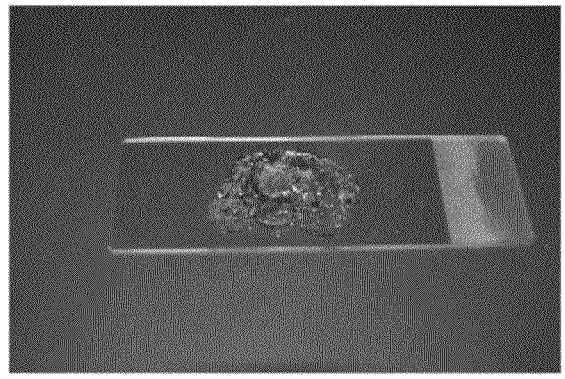
FIGS. 13(a), 13(b), and 13(c) are a photograph of a gel transferred to a slide glass, a photograph of a frozen gel, and a photograph of a slide glass whose entire surface is uniformly coated with a peptide gel, respectively.
Figure 13B:
Figure 13C:
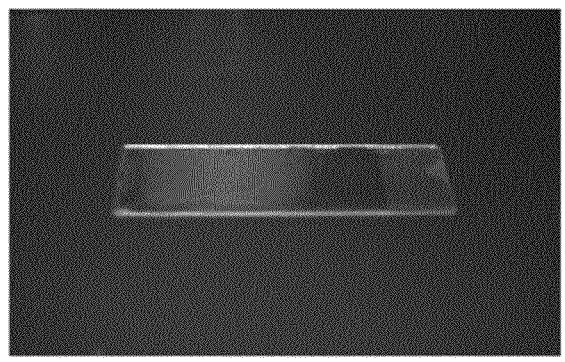

A slide glass whose entire surface was uniformly coated with a peptide gel was obtained in the same manner as in Example 9 except that a slide glass was used in place of the laboratory dish made of glass. FIG. 13(a), 13(b), and 13(c) show a photograph of the gel transferred to the slide glass, a photograph of the frozen gel, and a photograph of the slide glass whose entire surface was uniformly coated with the peptide gel, respectively.

INDUSTRIAL APPLICABILITY

The self-assembling peptide or the like of the present invention may be applied for regenerative medicine, a drug delivery system, a cosmetic, an artificial vitreous body, a hemostat, an injection for cosmetic surgery, bone filling, a joint lubricant, a water retention material for moistening, or the like.

Sequence Listing Free Text

SEQ ID NO: 1 is a self-assembling peptide of the present invention.
SEQ ID NO: 2 is a self-assembling peptide of the present invention.
SEQ ID NO: 3 is a modified peptide of the present invention.
SEQ ID NO: 4 is a peptide which is not a self-assembling peptide of the present invention.
SEQ ID NO: 5 is a peptide which is not a self-assembling peptide of the present invention.
SEQ ID NO: 6 is a self-assembling peptide of the present invention.
SEQ ID NO: 7 is a self-assembling peptide of the present invention.
SEQ ID NO: 8 is a self-assembling peptide of the present invention.
SEQ ID NO: 9 is a self-assembling peptide of the present invention.
SEQ ID NO: 10 is a self-assembling peptide of the present invention.
SEQ ID NO: 11 is a self-assembling peptide of the present invention.
SEQ ID NO: 12 is a modified peptide of the present invention.

The invention claimed is:

1. A self-assembling peptide, comprising an amino acid sequence: $a_1b_1c_1b_2a_2b_3db_4a_3b_5c_2b_6a_4$,
   wherein $a_1$ to $a_4$ each independently represent a basic amino acid residue,
   $b_1$ to $b_6$ in the amino acid sequence each independently represent an alanine residue, a valine residue, a leucine residue, or an isoleucine residue,
   $c_1$ and $c_2$ each independently represent an acidic amino acid residue, and
   d represents a hydrophobic amino acid residue.

2. The self-assembling peptide of claim 1,
   wherein d represents an alanine residue, a valine residue, a leucine residue, or an isoleucine residue.

3. The self-assembling peptide of claim 1,
   wherein the self-assembling peptide comprises a peptide comprising an amino acid sequence of RLDLRLALRLDLR (SEQ ID NO: 1), RLDLRLLLRLDLR (SEQ ID NO: 2), RADLRLALRLDLR (SEQ ID NO: 6), RLDLRLALRLDAR (SEQ ID NO: 7), RADLRLLLRLDLR (SEQ ID NO: 8), RADLRLLLRLDAR (SEQ ID NO: 9), RLDLRALLRLDLR (SEQ ID NO: 10), or RLDLRLLARLDLR (SEQ ID NO: 11).

4. The self-assembling peptide of claim 1,
   wherein the self-assembling peptide comprises a peptide comprising an amino acid sequence of RLDLRLALRLDLR(SEQ ID NO: 1) or RLDLRLLLRLDLR(SEQ ID NO: 2).

5. A modified peptide, comprising the self-assembling peptide of claim 1,
   wherein at least one of the N-terminal amino group and the C-terminal carboxyl group is modified, and
   the modified peptide has a self-assembling ability.

6. The modified peptide of claim 5,
   wherein the at least one of the N-terminal amino group and the C-terminal carboxyl group is modified with an amino acid sequence comprising RGD.

7. A peptide gel, which is formed from an aqueous solution comprising at least one member selected from the group consisting of:
   the self-assembling peptide of claim 1, and
   a modified peptide, comprising the self-assembling peptide,
   in which at least one of the N-terminal amino group and the C-terminal carboxyl group is modified,
   wherein the modified peptide has a self-assembling ability.

8. The peptide gel of claim 7, wherein the aqueous solution further comprises an additive.

9. The peptide gel of claim 8,
   wherein the additive comprises at least one member selected from the group consisting of a pH adjuster, an amino acid, a vitamin, a saccharide, a polysaccharide, an alcohol, a polyalcohol, a pigment, a bioactive substance, an enzyme, an antibody, DNA, and RNA.

10. The peptide gel of claim 7,
    wherein the peptide gel has an absolute value L (g/s) of an amount of change in load per unit time of 0.03 g/s or more in an approximate straight line of values measured from a start of compression to between 8 and 10 seconds in a compression test carried out at a compression speed of 0.05 mm/s with a jig whose tip has a spherical shape with a diameter of 3.2 mm and a curvature radius of 1.6 mm under a temperature condition of 22° C.

11. A substrate, comprising at least one selected from the group consisting of:
    (i) the self-assembling peptide of claim 1,
    (ii) a modified peptide, comprising the self-assembling peptide,
    in which at least one of the N-terminal amino group and the C-terminal carboxyl group is modified, and
    wherein the modified peptide has a self-assembling ability, and
    (iii) a peptide gel, which is formed from an aqueous solution comprising at least one selected from the group consisting of:
    the self-assembling peptide; and
    the modified peptide
    wherein the substrate is suitable for a cell culture.

12. A method for manufacturing a sterile peptide, comprising:
    sterilizing at least one member selected from the group consisting of
    the self-assembling peptide of claim 1, and
    a modified peptide, comprising the self-assembling peptide,
    in which at least one of the N-terminal amino group and the C-terminal carboxyl group is modified, and
    wherein the modified peptide has a self-assembling ability,
    under a pressurized condition at 100° C. or more.

13. A method for manufacturing an article coated with a peptide gel, comprising:
    freezing the peptide gel of claim 7, to obtain a frozen peptide gel;
    melting the frozen peptide gel to provide a peptide sol;
    coating at least part of a surface of an article with the peptide sol; and
    reconstructing a peptide gel from the peptide sol.

* * * * *